United States Patent
Besenmatter et al.

(10) Patent No.: US 9,951,306 B2
(45) Date of Patent: Apr. 24, 2018

(54) CATALASE IN GROWTH MEDIA

(71) Applicant: EUCODIS BIOSCIENCE GMBH, Vienna (AT)

(72) Inventors: Werner Besenmatter, Wiener Neudorf (AT); Axel Niebisch, Vienna (AT); Jan Modregger, Brunn am Gebirge (AT); Bhupinder Hundle, Worcestershire (GB)

(73) Assignee: Eucodis Bioscience GmbH, Vienna (AT)

( * ) Notice: Subject to any disclaimer, the term of this patent is extended or adjusted under 35 U.S.C. 154(b) by 105 days.

(21) Appl. No.: 14/407,772

(22) PCT Filed: Jun. 12, 2013

(86) PCT No.: PCT/EP2013/062132
§ 371 (c)(1),
(2) Date: Dec. 12, 2014

(87) PCT Pub. No.: WO2013/186253
PCT Pub. Date: Dec. 19, 2013

(65) Prior Publication Data
US 2015/0152466 A1 Jun. 4, 2015

(30) Foreign Application Priority Data
Jun. 13, 2012 (EP) .................................... 12171798

(51) Int. Cl.
| | |
|---|---|
| *C12N 1/20* | (2006.01) |
| *C12Q 1/04* | (2006.01) |
| *C12Q 1/18* | (2006.01) |
| *C12Q 1/22* | (2006.01) |
| *C12N 9/08* | (2006.01) |
| *C12Q 1/30* | (2006.01) |

(52) U.S. Cl.
CPC ............. *C12N 1/20* (2013.01); *C12N 9/0065* (2013.01); *C12Q 1/045* (2013.01); *C12Q 1/18* (2013.01); *C12Q 1/22* (2013.01); *C12Q 1/30* (2013.01); *C12Y 111/01006* (2013.01)

(58) Field of Classification Search
CPC . C12Q 1/30; C12Q 1/045; C12Q 1/22; C12Q 1/18; C12N 9/0065; C12N 1/20; C12Y 111/01006
See application file for complete search history.

(56) References Cited

U.S. PATENT DOCUMENTS

| | | | | |
|---|---|---|---|---|
| 4,419,449 A | * | 12/1983 | Maillard | A61K 35/74 435/170 |
| 5,571,719 A | * | 11/1996 | Christensen | A61L 12/126 134/901 |
| 6,319,695 B1 | * | 11/2001 | Wong | C07H 3/06 435/84 |

FOREIGN PATENT DOCUMENTS

| | | |
|---|---|---|
| EP | 2256192 | 12/2010 |
| GB | 1478238 | 6/1977 |

OTHER PUBLICATIONS

"Sodium Pyruvate." Chemical Book. [online]. 2016. [retrieved on Sep. 30, 2016]. Retrieved from the Internet: <URL: http://www.chemicalbook.com/ChemicalProductProperty_EN_CB4252757.htm>). 3 pages.*
Burton, SD et al. Effect of catalase and cultural conditions on growth of Beggiatoa. Journal of Bacteriology. 1964. 88(6): 1755-1761.*
Nelson, DC et al. Organic Nutrition of *Beggiatoa* sp. Journal of Bacteriology. 1981. 147(1): 236-247.*
Padgett, PJ et al. The microaerophile Spirillum volutans: cultivation on complex liquid and solid media. Applied and Environmental Microbiology. 1982. 43(2): 469-477.*
Podkopaeva, DA et al. Oxidative stress and antioxidant cell protection systems in the microaerophilic bacterium Spirillum winogradskii. Microbiology. 2003. 72(5): 534-541.*
Xu, Y. et al. Sulfur geochemistry of hydrothermal waters in Yellowstone National Park: I. The origin of thiosulfate in hot spring waters. Geochimica et Cosmochimica Acta. 1998. 62(23/24): 3729-3743.*
"Sodium Pyruvate Solution." [online]. No date provided. Applied Biological Materials, Inc. [retrieved on Aug. 2, 2017]. Retrieved from the Internet: URL: https://www.abmgood.com/Documents/files/TM057:20Datasheet.pdf.*
Zamocky M et al., The Journal of Biological Chemistry, vol. 287, No. 38, pp. 32254-32262, 2012.
International Search Report, International Patent Application No. PCT/EP2013/062132, dated Jul. 10, 2013.
International Written Opinion, International Patent Application No. PCT/EP2013/062132, dated Jul. 10, 2013.
International Preliminary Report on Patentability, International Patent Application No. PCT/EP2013/062132, dated Dec. 16, 2014.
Partial European Search Report, European Patent Application No. 12171798.7-1223, dated Oct. 1, 2012.

(Continued)

*Primary Examiner* — Renee Claytor
*Assistant Examiner* — Susan E. Fernandez
(74) *Attorney, Agent, or Firm* — Loza & Loza, LLP; Michael Fedrick

(57) ABSTRACT

The present invention relates to the use of a secreted fungal catalase, for hydrogen-peroxide neutralization in growth media for the detection of microorganisms as well as to a method for detecting microorganisms in hydrogen peroxide-bearing aerosol or on a hydrogen peroxide bearing surface, said method comprising contacting said aerosol or surface with a growth medium comprising a secreted fungal catalase, and detecting growth of microorganisms in said medium.

10 Claims, 1 Drawing Sheet

(56) References Cited

OTHER PUBLICATIONS

Calabrese and Bissonnette, Canadian Journal of Microbiology, 1990, 36:544-550.
Harmon et al., Applied and Environmental Microbiology, vol. 32, No. 3, 1976, pp. 409-416.
McDonald, et al., Applied and Environmental Microbiology, 1983, 45:360-365.
Ohresser et al., PDA J Pharm Sci Technol., 2004, 58:75-80.
Switala and Loewen, Archives of Biochemistry and Biophysics, 2002, 401:145-154.
Zamocky et al., Biochemie 2012, 94(3):673-683.
Extended European Search Report, European Patent Application No. 12171798.7-1223, dated Jan. 30, 2013.

* cited by examiner

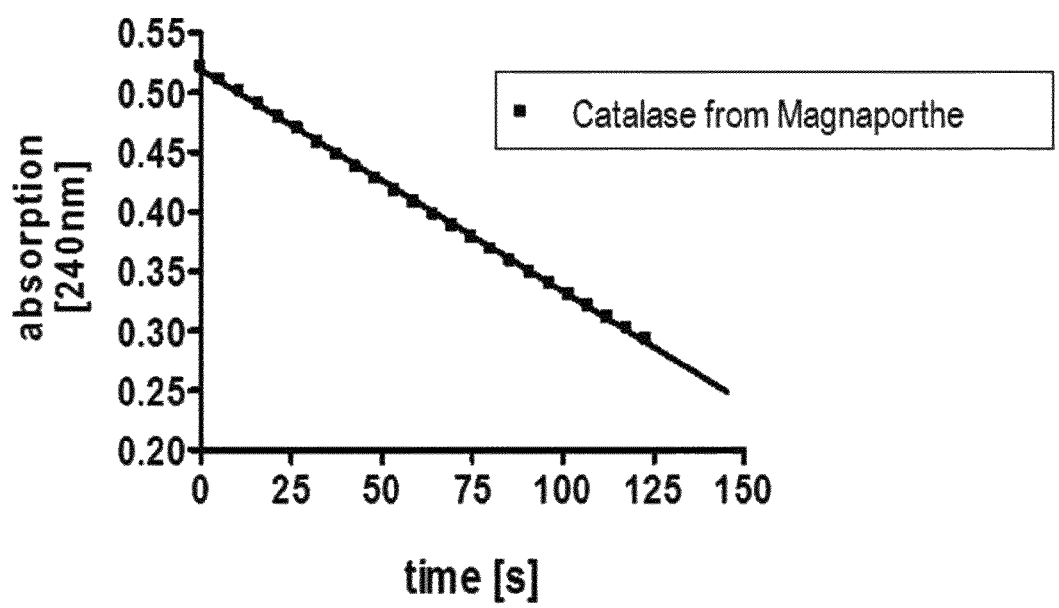

CATALASE IN GROWTH MEDIA

CROSS-REFERENCE TO RELATED APPLICATIONS

This application is the U.S. national stage of International Patent Application No. PCT/EP2013/062132, filed on Jun. 12, 2013 and entitled CATALASE IN GROWTH MEDIA, which claims the benefit of priority under 35 U.S.C. § 119 from European Patent Application No. 12171798.7, filed Jun. 13, 2012. The disclosures of the foregoing applications are incorporated herein by reference in their entirety.

BACKGROUND OF THE INVENTION

Hydrogen peroxide is used as a potent disinfectant for a broad range of microorganisms, but does not necessarily eliminate all microorganisms during the application time. To check if microorganisms survived the treatment with hydrogen peroxide, suitable growth media are applied. However, remaining hydrogen peroxide inhibits the growth of microorganisms, which leads to false negative results and a false sense of security. Thus hydrogen peroxide needs to be neutralized or degraded in growth media. For this purpose, different additives to growth media have been suggested, such as for example pyruvate or catalase.

Pyruvate reacts with hydrogen peroxide to acetate, carbon dioxide and water. One disadvantage of pyruvate and other chemical additives compared to a catalytic degradation is that the chemical additives are used up by the neutralizing reaction with hydrogen peroxide. Another disadvantage of pyruvate is that microorganisms can metabolize pyruvate. McDonald, et al. (Applied and Environmental Microbiology, 1983, pp 360-365) tested pyruvate addition to violet red bile agar, which is selective for coliforms, and showed that pyruvate lead to false-positive results.

Catalases catalyze the degradation of hydrogen peroxide to the harmless products water and oxygen. Catalases, especially the longest known catalase from bovine liver, have been tried before in growth media, specifically agar plates, with limited success. Calabrese and Bissonnette (Canadian Journal of Microbiology, 1990 pp 544-550) combined bovine liver catalase, 1500 U/plate and sodium pyruvate 5 g/l in agar growth media to increase the recovery of bacteria stressed by acidic water. Ohresser et al. (PDA J Pharm Sci Technol., 2004 pp 75-80) found only 60% recovery with 8000 international units of catalase per plate and stated that "high concentrations of enzyme in the media were not economically viable (in terms of cost per plate)". Ohresser et al. and McDonald et al. report the unsuccessful application of a catalase in agar plates. These and other reports do not specify the source organism of the catalase, and thus imply that the source of a catalase is not important or it does not make a difference. Harmon and Kautter (Appl Environ Microbiol. 1976 September; 32(3):409-16) describe that catalases from sources other than beef liver were effective in stimulating growth of *C. perfringens* on different media. The catalase solutions were spread on the surface of the plates because of the low thermal stability of the enzyme.

However, Switala and Loewen (Archives of Biochemistry and Biophysics, 2002 pp 145-154) showed the diversity of properties among catalases, e.g. a broad range of sensitivities to heat inactivation and a wide range of $K_m$ values was observed. A catalase with a low value for $K_m$ (the calculated Michaelis constant) is desirable in an application with low hydrogen peroxide concentrations.

SUMMARY OF THE INVENTION

Previously unanticipated, the inventors have surprisingly found that a class of catalases is especially effective in applications in growth media. This class comprises enzymes that are derived from extracellular fungal catalases. Originally, these catalases evolved in nature for secretion and function outside the fungal cell. This makes them also useful for industrial applications outside the original cells.

For the successful application in growth media, a catalase needs to be stable during production and storage of the growth media. A catalase can be added during the production of agar media when it is cooled down to 50° C. before the agar medium solidifies. Thus, it is advantageous if a catalase used according to the invention is sufficiently stable at 50° C. However, a catalase used according to the invention can be added to an agar medium at temperatures below 50° C., for example by adding a catalase onto an agar plate after the agar solidified, or by adding a catalase to a growth medium that does not contain agar. Sometimes, growth media are gamma-irradiated to ensure sterility before they are put to use. Thus, a catalase as used according to the invention also should be sufficiently stable during gamma-irradiation. Furthermore, a catalase as used according to the invention must be sufficiently stable in a growth medium during storage, before it is used.

During the usage of catalase in agar plates, hydrogen peroxide is degraded to oxygen, which diffuses away. Especially if highly concentrated hydrogen peroxide is added, oxygen may be produced within the agar at such fast rates that gaseous oxygen causes small bubbles and cracks within the agar within less than one hour. An untrained observer may mistake the formed bubbles and cracks with colonies, which look different and appear later during incubation over night. Although Ohresser et al. observed this phenomenon of bubbles and cracks before, no solution has been reported yet. Previously unanticipated, the inventors have surprisingly found that chemical additives in combination with a catalase prevent the formation of cracks and bubbles effectively.

An object of the present invention is an optionally sterilized medium for the detection of microorganisms in hydrogen-bearing environments like surfaces or air, which do not suffer from the above indicated disadvantages and which affords enhanced results.

Accordingly, as first aspect the invention provides a hydrogen-peroxide neutralizing medium comprising at least 0.3 U/ml of a secreted fungal catalase.

A further aspect of the invention is a medium as described above further comprising up to 0.05 g/l, preferably up to 0.005 g/l sodium thiosulfate.

A further aspect of the invention is a hydrogen-peroxide neutralizing agar medium comprising at least 0.3 U/ml of a catalase and further comprising up to 4 g/l, preferably up to 2 g/l, more preferably up to 0.2 g/l sodium pyruvate to prevent the formation of cracks or bubbles in the agar medium after the addition of hydrogen peroxide.

A further aspect of the invention is a medium as described above further comprising up to 0.05 g/l, preferably up to 0.005 g/l sodium thiosulfate.

A further aspect of the invention is a medium as described above, wherein said medium is sterilized, preferably sterilized by gamma-irradiation.

A further aspect of the invention is a medium as described above, wherein said catalase is derived from a species of

*Magnaporthe* or *Scytalidium*, preferably from *Magnaporthe grisea* or from *Scytalidium thermophilum*.

A further aspect of the invention is the use of a secreted fungal catalase, for hydrogen-peroxide neutralization in a medium for the detection of microorganisms.

A further aspect of the invention is the use as described above, wherein the catalase is derived from a species of *Magnaporthe* or *Scytalidium*, preferably from *Magnaporthe grisea* or from *Scytalidium thermophilum*.

A further aspect of the invention is the use as described above, wherein the catalase exhibits an activity of at least 25%, preferably of at least 35%, more preferred of at least 50% after incubation at 50° C. for 4 h.

A further aspect of the invention is the use as described above, wherein the catalase exhibits an activity of at least 25%, preferably of at least 35%, more preferred of at least 50% after sterilization of the medium by gamma-irradiation with at least 10 kGy, preferably at least 15 kGy, more preferably at least 20 kGy.

A further aspect of the invention is the use as described above, wherein the catalase exhibits an activity of at least 25%, preferably of at least 35%, more preferred of at least 50% after storage in the medium for at least 6 months.

A further aspect of the invention is the use as described above, wherein the catalase is used in a concentration of about 0.3 to 90 Um/l medium.

A further aspect of the invention is the use as described above, comprising up to 4 g/l, preferably up to 2 g/l, more preferably up to 0.2 g/l sodium pyruvate and optionally up to 0.05 g/l, preferably up to 0.005 g/l sodium thiosulfate.

A further aspect of the invention is a method for detecting microorganisms in a hydrogen peroxide-bearing aerosol or on a hydrogen peroxide-bearing surface, said method comprising contacting said aerosol or surface with a medium as described above, and detecting growth of microorganisms in said medium.

A further aspect of the invention is a method as described above comprising the steps of a. bringing a hydrogen peroxide-bearing aerosol or a hydrogen peroxide-bearing surface into contact with a growth medium comprising the catalase as described above;
b. placing the growth medium in an environment allowing the development of colonies of microorganisms;
c. determining if colonies of microorganisms which may have developed during step (b) are present.

A further aspect of the invention is a method as described above, wherein the hydrogen peroxide-bearing aerosol comprises air.

DETAILED DESCRIPTION OF THE INVENTION

In the context of this invention the term “aerosol” is defined as a gas that may contain solid particles and/or liquid droplets and/or biological cells and/or spores and/or conidia and/or virus particles.

In the context of this invention the term “secreted fungal catalase” is defined as an enzyme that derived from a catalase that originated from a fungus that secreted said catalase. The secreted fungal catalase can be isolated from its original fungus, or it can be produced as secreted or as intracellular protein in an expression host, for example *Escherichia coli, Bacillus subtilis, Pichia pastoris, Aspergillus oryzae*. A gene encoding a catalase according to the invention can be derived from a natural fungal gene or from a synthetic gene with sequence information from a fungal gene. Examples of fungi where said secreted fungal catalase or its gene can originate from are *Magnaporthe grisea* (*Pyricularia grisea, Magnaporthe oryzae*), *Scytalidium thermophilum, Humicola insolens, Trichoderma atroviride, Colletotrichum graminicola, Nectria haematococca, Gibberella zeae* (*Fusarium graminearum*), *Fusarium oxysporum, Gibberella moniliformis, Cryphonectria parasitica, Claviceps purpurea, Oidiodendron maius, Phytophthora sojae, Pythium ultimum, Thielavia terrestris* (*Acremonium alabamense*), *Verticillium albo-atrum* or *Verticillium dahliae.*

The term “medium” refers to a sterilisabel growth or nutrient medium designed to support the growth of microorganisms. The most common growth media for microorganisms are nutrient broths and agar plates. Microorganisms can grow in liquid growth media and on the surface of solid growth media.

Surprisingly, the hydrogen peroxide-neutralising action of the media according to the invention can be boosted by the addition of at least 40 U/plate of a secreted fungal catalase; optionally sodium pyruvate and/or sodium thiosulfate are added in small amounts.

Media according to the invention with the addition of a secreted fungal catalase and optionally sodium pyruvate and/or sodium thiosulfate are stable for 6 month, which substantially facilitates storage and shipping and guarantees that the customer has a long potential period of use.

The subject matter of the following definitions is considered embodiments of the present invention:

1. A hydrogen-peroxide neutralizing medium comprising at least 0.3 U/ml of a secreted fungal catalase.

2. The medium according to claim 1 further comprising up to 4 g/l, preferably up to 2 g/l, more preferably up to 0.2 g/l sodium pyruvate.

3. The medium according to claim 2, wherein said pyruvate prevents the formation of cracks or bubbles in the agar medium after the addition of hydrogen peroxide.

4. The medium according to any one of claim 1 or 3 further comprising up to 0.05 g/l, preferably up to 0.005 g/l sodium thiosulfate.

5. The medium according to any one of claims 1 to 4, wherein said medium is sterilized, preferably gamma-irradiated.

6. The medium according to any one of claims 1 to 5, wherein said catalase is derived from a species of *Magnaporthe* or *Scytalidium*, preferably from *Magnaporthe grisea* or from *Scytalidium thermophilum.*

7. Use of a secreted fungal catalase, for hydrogen-peroxide neutralization in a medium for the detection of microorganisms.

8. The use according to claim 7, wherein the catalase is derived from a species of *Magnaporthe or Scytalidium*, preferably from *Magnaporthe grisea* or from *Scytalidium thermophilum.*

9. The use according to claim 7 or 8, wherein the catalase exhibits an activity of at least 25%, preferably of at least 35%, more preferred of at least 50% after incubation at 50° C. for 4 h.

10. The use according to any one of claims 7 to 9, wherein the catalase exhibits an activity of at least 25%, preferably of at least 35%, more preferred of at least 50% after sterilization of the medium by gamma-irradiation with at least 10 kGy, preferably at least 15 kGy, more preferably at least 20 kGy.

11. The use according to any one of claims 7 to 10, wherein the catalase exhibits an activity of at least 25% preferably of at least 35%, more preferred of at least 50% after storage in the medium for at least 6 months.

12. The use according to any one of claims 7 to 11, wherein the catalase is used in a concentration of about 0.3 to 90 U/ml medium.

13. The use according to any one of claims 7 to 12, comprising up to 4 g/l, preferably up to 2 g/l, more preferably up to 0.2 g/l sodium pyruvate and optionally up to 0.05 g/l, preferably up to 0.005 g/l sodium thiosulfate.

14. A method for detecting microorganisms in hydrogen peroxide-bearing aerosol or on a hydrogen peroxide-bearing surface, said method comprising contacting said aerosol or surface with a medium according to any one of claims 1 to 6, and detecting growth of microorganisms in said medium.

15. The method according to claim 14 comprising the steps of
   a. bringing a hydrogen peroxide-bearing aerosol or a hydrogen peroxide-bearing surface into contact with a growth medium comprising the catalase according to any one of claims 1 to 6;
   b. placing the growth medium in an environment allowing the development of colonies of microorganisms;
   c. determining if colonies of microorganisms which may have developed during step (b) are present.

16. The method according to claim 14 or 15, wherein the hydrogen peroxide-bearing aerosol comprises air.

Example 1 Preparation of Agar Plates

TABLE 1

Components of TSA-LT agar growth medium

| Ingredient | g/l |
|---|---|
| Casein peptone | 15.0 |
| Soy peptone | 5.0 |
| Sodium chloride | 5.0 |
| Agar | 15.0 |
| Lecithin | 0.7 |
| Tween80 | 5.0 |

TSA-LT Stands for Tryptic Soy Agar with Lecithin and Tween.

TSA-LT agar growth medium was prepared by adding into each half-liter screw-cap bottle 16 g CASO agar powder, which contains the first four components of Table 1 premixed, 0.28 g lecithin, 2 g Tween80 and 400 ml pure water. After autoclaving at 121° C. for 20 minutes, the medium was cooled down to 50° C. in a water bath. Catalase solutions, or other solutions with additives, were added with sterile filtration. After mixing, 30 ml growth medium were poured into each petri dish with a diameter of 90 millimeter. The next day the agar plates were packed in plastic foil and some plates were gamma-irradiated with 20.5 kGy.

Catalase solutions were prepared as described below, sterile filtered, stored at 4° C. and their concentration measured as described in Example 4.

Catalase from *Magnaporthe* was prepared as described (and called MagKatG2) by Zámocký et al. (Biochimie, 2012, pp 673-683) and the purification process stopped before the hydroxyapatite column.

Catalase from *Scytalidium* was prepared from the commercial product (Terminox Ultra 50 L from Novozymes) by ultrafiltration with a 30,000 MWCO (Molecular Weight Cut Off) and buffer exchange to 0.1 M potassium phosphate with 0.1 M sodium chloride at a pH of 7.0.

Catalase from bovine liver was prepared from the commercial product (C9322 from Sigma) by dissolving in 0.1 M potassium phosphate at a pH of 7.0.

Example 2 Agar Diffusion Test

TABLE 2

Components of LB-T growth medium

| Ingredient | g/l |
|---|---|
| Tryptone | 10.0 |
| Yeast extract | 5.0 |
| Sodium chloride | 5.0 |
| Tween20 | 5.0 |

*Bacillus subtilis* ATCC 6633 was grown in LB-T growth medium (see Table 2) overnight at 37° C. The *Bacillus* suspension was diluted with LB-T growth medium to an OD600 (optical density at 600 nm) of approximately 0.1. This diluted *Bacillus* suspension (200 μl/plate) was spread onto dry TSA-LT agar plates from Example 1. Four paper discs were put onto each agar plate. The paper discs had a diameter of 6 mm and were prepared from gel blot paper GB003 from Whatman with a hole punch. 10 μl of an aqueous solution that contained hydrogen peroxide at a concentration of 2%, 5%, 8% and 10%, respectively, were pipetted onto the four paper discs on each agar plate. Afterwards the plates were incubated overnight at 37° C. The diameter of the inhibition zone was measured and the diameter of the paper disc subtracted and the result divided by two. Thus a reported value in the following table is the distances from the edge of the paper disc to the end of the inhibition zone. A value of zero means no inhibition observed. The larger the value, the stronger the undesired inhibition.

TABLE 3

Inhibition on agar plates

| Additives | Concentration | mm (2%) | mm (5%) | mm (8%) | mm (10%) |
|---|---|---|---|---|---|
| Catalase from *Magnaporthe* | 300 U/plate | 0 | 0 | 0 | 0.5 |
| Catalase from *Magnaporthe* | 150 U/plate | 0 | 0 | 0.5 | 1 |
| Catalase from *Magnaporthe* | 80 U/plate | 0 | 0.5 | 1.5 | 2.5 |
| Catalase from *Magnaporthe* | 40 U/plate | 0 | 2 | 3.5 | 4 |
| Catalase from *Magnaporthe* | 20 U/plate | 0 | 3.5 | 5 | 5.5 |
| Catalase from *Magnaporthe* | 10 U/plate | 1.5 | 5 | 6 | 7 |
| Catalase from *Scytalidium* | 300 U/plate | 0 | 0 | 0 | 0.5 |
| Catalase from *Scytalidium* | 150 U/plate | 0 | 0 | 0.5 | 1 |
| Catalase from *Scytalidium* | 80 U/plate | 0 | 0.5 | 1.5 | 2 |
| Catalase from *Scytalidium* | 40 U/plate | 0 | 1.5 | 2.5 | 3.5 |
| Catalase from *Scytalidium* | 20 U/plate | 0 | 3 | 4 | 5 |
| Catalase from *Scytalidium* | 10 U/plate | 1 | 4.5 | 5.5 | 6. |
| Catalase from bovine liver | 300 U/plate | 0 | 2 | 4 | 4.5 |
| Catalase from bovine liver | 150 U/plate | 0.5 | 4 | 5 | 6 |
| Catalase from bovine liver | 80 U/plate | 1 | 5 | 6 | 7 |
| Sodium pyruvate | 2.00 g/l | 0 | 1 | 2 | 2.5 |
| Sodium thiosulfate | 0.05 g/l | | | | |
| Without additives | | 4.5 | 7 | 8 | 8.5 |

TABLE 4

Inhibition on gamma-irradiated agar plates

| Additives | Concentration | mm (2%) | mm (5%) | mm (8%) | mm (10%) |
|---|---|---|---|---|---|
| Catalase from *Magnaporthe* | 300 U/plate | 0 | 0 | 0.5 | 0.5 |
| Catalase from *Magnaporthe* | 150 U/plate | 0 | 0.5 | 1 | 2 |
| Catalase from *Magnaporthe* | 80 U/plate | 0 | 1 | 2.5 | 3 |
| Catalase from *Magnaporthe* | 40 U/plate | 0 | 3 | 4.5 | 4.5 |
| Catalase from *Magnaporthe* | 20 U/plate | 0.5 | 4.5 | 5.5 | 6 |
| Catalase from *Magnaporthe* | 10 U/plate | 1.5 | 5.5 | 7 | 7.5 |
| Catalase from *Scytalidium* | 300 U/plate | 0 | 0 | 0.5 | 0.5 |
| Catalase from *Scytalidium* | 150 U/plate | 0 | 0 | 0.5 | 1.5 |
| Catalase from *Scytalidium* | 80 U/plate | 0 | 1 | 1.5 | 2.5 |
| Catalase from *Scytalidium* | 40 U/plate | 0 | 2.5 | 3.5 | 4 |
| Catalase from *Scytalidium* | 20 U/plate | 0.5 | 3.5 | 5 | 5.5 |
| Catalase from *Scytalidium* | 10 U/plate | 1.5 | 5.5 | 7 | 7.5 |
| Catalase from bovine liver | 300 U/plate | 1.5 | 5.5 | 6.5 | 7.5 |
| Catalase from bovine liver | 150 U/plate | 2 | 6 | 7.5 | 8 |
| Catalase from bovine liver | 80 U/plate | 3.5 | 7 | 8 | 8.5 |
| Sodium pyruvate | 2.00 g/l | 0 | 1 | 2 | 3 |
| Sodium thiosulfate | 0.05 g/l | | | | |
| Without additives | | 4.5 | 7.5 | 8.5 | 9 |

Because 30 ml growth medium was used per plate, a concentration of 300 U/plate equals 10 U/ml, 40 U/plate equals 1.3 U/ml. and 10 U/plate equals 0.3 U/ml.

Example 3 Growth Promotion Test

*Bacillus subtilis* ATCC 6633 was grown in LB-T growth medium (see Table 2) overnight at 37° C. The *Bacillus* suspension was put on ice and diluted to an OD600 of approximately 0.1 with a PBS solution that has a pH of 7.4 and contains 8 g/l sodium chloride, 0.2 g/l potassium chloride, 0.2 g/l potassium dihydrogen phosphate and 0.918 g/l disodium hydrogen phosphate. This diluted *Bacillus* suspension was further diluted 10,000 times with the PBS solution and kept on ice. Meanwhile, 300 µl 1% hydrogen peroxide solution was spread onto a dry plate, which contains 30 ml TSA-LT agar growth medium (see Example 1). Thus a concentration in the growth medium of 100 ppm (parts per million) hydrogen peroxide was applied. The plate was dried for 20 minutes at room temperature (20-25° C.). Then 200 µl 10,000 times diluted *Bacillus* suspension was spread onto the agar plate. Afterwards the plates were incubated overnight at 37° C.

TABLE 5

Colonies on agar plates

| Additives | Concentration | CFU* |
|---|---|---|
| Catalase from *Magnaporthe* | 300 U/plate | 189 |
| Catalase from *Magnaporthe* | 150 U/plate | 210 |
| Catalase from *Magnaporthe* | 80 U/plate | 169 |
| Catalase from *Magnaporthe* | 40 U/plate | 140 |
| Catalase from *Magnaporthe* | 20 U/plate | 8 |
| Catalase from *Magnaporthe* | 10 U/plate | 0 |
| Catalase from *Scytalidium* | 300 U/plate | 163 |
| Catalase from *Scytalidium* | 150 U/plate | 178 |
| Catalase from *Scytalidium* | 80 U/plate | 162 |
| Catalase from *Scytalidium* | 40 U/plate | 154 |
| Catalase from *Scytalidium* | 20 U/plate | 6 |
| Catalase from *Scytalidium* | 10 U/plate | 0 |
| Catalase from bovine liver | 300 U/plate | 0 |
| Catalase from bovine liver | 150 U/plate | 0 |
| Catalase from bovine liver | 80 U/plate | 0 |
| Sodium pyruvate | 2.00 g/l | 161 |
| Sodium thiosulfate | 0.05 g/l | |
| Without additives | | 0 |
| Without additives and $H_2O_2$ | | 164 |

*CFU stands for colony-forming units.

TABLE 6

Colonies on gamma-irradiated agar

| Additives | Concentration | CFU |
|---|---|---|
| Catalase from *Magnaporthe* | 300 U/plate | 205 |
| Catalase from *Magnaporthe* | 150 U/plate | 190 |
| Catalase from *Magnaporthe* | 80 U/plate | 171 |
| Catalase from *Magnaporthe* | 40 U/plate | 58 |
| Catalase from *Magnaporthe* | 20 U/plate | 1 |
| Catalase from *Magnaporthe* | 10 U/plate | 0 |
| Catalase from *Scytalidium* | 300 U/plate | 161 |
| Catalase from *Scytalidium* | 150 U/plate | 205 |
| Catalase from *Scytalidium* | 80 U/plate | 109 |
| Catalase from *Scytalidium* | 40 U/plate | 6 |
| Catalase from *Scytalidium* | 20 U/plate | 0 |
| Catalase from *Scytalidium* | 10 U/plate | 0 |
| Catalase from bovine liver | 300 U/plate | 0 |
| Catalase from bovine liver | 150 U/plate | 0 |
| Catalase from bovine liver | 80 U/plate | 0 |
| Sodium pyruvate | 2.00 g/l | 229 |
| Sodium thiosulfate | 0.05 g/l | |
| Without additives | | 0 |

As shown in Table 5, catalase from *Magnaporthe* and catalase from *Scytalidium* at concentrations of 40 U/plate and at higher concentrations in not irradiated medium, lead to a recovery of much more than 50% of the applied colony forming units. However, catalase from bovine liver, even at the highest tested concentration of 300 U/plate, leads to 0% recovery of the applied colony forming units.

As shown in table 6, catalase from *Magnaporthe* and catalase from *Scytalidium* at concentrations of 80 U/plate and at higher concentrations in gamma-irradiated medium, lead to a recovery of more than 50% of the applied colony forming units. After gamma-irradiation, agar plates that contain catalase from *Magnaporthe* or catalase from *Scytalidium* remain effective in degrading hydrogen peroxide.

Example 4 Measurement of Catalase Activity

The definition of 1 catalase unit (1 U) is the amount of enzyme decomposing 1 micromole of hydrogen peroxide per minute at 25° C. at a pH of 7.0 and with an initial hydrogen peroxide concentration of 0.010 M (M stands for molar, which is mol/l).

The pH of 7.0 was ensured with a 0.1 M phosphate buffer, which was prepared by mixing 61.5 ml 1 M dipotassium hydrogen phosphate and 38.5 ml 1 M potassium dihydrogen phosphate with 900 ml pure water. A 0.01034 M hydrogen peroxide solution was prepared by mixing 42.3 µl 30 weight % hydrogen peroxide solution, which has a density of 1.11 g/ml, with 40 ml 0.1 M phosphate buffer. The temperature was brought to 25° C. in a water bath, and 2.9 ml of this solution was pipetted into a quartz cuvette. Then 100 µl diluted catalase solution was added, mixed and the kinetic measurement quickly started. The absorption decrease per minute was measured with a photometer at 240 nm within the first minute in the linear range.

Before this measurement, catalase solutions were diluted with 0.1 M phosphate buffer. Different dilutions were prepared, for example with a dilution factor of 20, 50 and 100. The dilution with the factor 20 was prepared by mixing 50 µl catalase solution with 950 µl 0.1 M phosphate buffer. The catalase dilution that gave around 0.1 absorption decrease per minute was used for the following calculation. The absorption decrease per minute was multiplied with the catalase dilution factor and multiplied with 688, which gives the concentration in the undiluted catalase solution in U/ml. The factor 688 includes the extinction coefficient (43.6 $M^{-1}cm^{-1}$) of hydrogen peroxide at 240 nm and the dilution in the cuvette.

FIG. 1: shows the measurement of the activity of *Magnaporthe* catalase

Example 5 Crack formation Test

Equal amounts of hydrogen peroxide, either 100 µl 3% or 300 µl 1% hydrogen peroxide were spread onto dry agar plates, which were prepared as described in Example 1 without gamma-irradiation. Then the plates were dried for 20 minutes at room temperature (20-25° C.). Afterwards 200 µl sterile PBS solution, which was prepared as described in Example 3, were spread onto the agar plate. The plates were incubated overnight at 37° C.

TABLE 7

Crack formation in agar plates and its prevention

| Additives | Concentration | Cracks and bubbles 100 µl 3% $H_2O_2$ | Cracks and bubbles 100 µl 1% $H_2O_2$ |
|---|---|---|---|
| Catalase from *Magnaporthe* | 338 U/plate | many | 0 |
| Catalase from *Magnaporthe* | 75 U/plate | many | 0 |
| Catalase from *Scytalidium* | 338 U/plate | many | few |
| Catalase from *Scytalidium* | 75 U/plate | many | few |
| Catalase from *Magnaporthe* sodium pyruvate sodium thiosulfate | 75 U/plate 2.00 g/l 0.05 g/l | 0 | 0 |
| Catalase from *Magnaporthe* sodium pyruvate sodium thiosulfate | 75 U/plate 0.20 g/l 0.005 g/l | 0 | 0 |
| Catalase from *Scytalidium* sodium pyruvate sodium thiosulfate | 75 U/plate 2.00 g/l 0.05 g/l | 0 | 0 |
| Catalase from *Scytalidium* sodium pyruvate sodium thiosulfate | 75 U/plate 0.20 g/l 0.005 g/l | 0 | 0 |

The formation of cracks and bubbles was completely prevented by the addition of pyruvate, even at low concentrations of pyruvate.

Even if the same amount of hydrogen peroxide per plate had been applied, fewer cracks were formed with a more diluted solution of hydrogen peroxide. Furthermore we observed that cracks predominantly appeared in that part of the agar plated, where the hydrogen peroxide had been first applied before it was spread on the whole agar surface.

Example 6 Growth Promotion Test, Further Examples

As described in Example 3, growth promotion tests were conducted with the agar plates as used in Example 5.

TABLE 8

Colonies and cracks on agar

| Additives | Concentration | CFU | Cracks and bubbles |
|---|---|---|---|
| Catalase from *Magnaporthe* | 338 U/plate | 137 | 1-2 |
| Catalase from *Magnaporthe* | 75 U/plate | 97 | 1-2 |
| Catalase from *Scytalidium* | 338 U/plate | 83 | 3-4 |
| Catalase from *Scytalidium* | 75 U/plate | 68 | 3-4 |
| Catalase from *Magnaporthe* sodium pyruvate sodium thiosulfate | 75 U/plate 2.00 g/l 0.05 g/l | 120 | 0 |
| Catalase from *Magnaporthe* sodium pyruvate sodium thiosulfate | 75 U/plate 0.20 g/l 0.005 g/l | 108 | 0 |
| Catalase from *Scytalidium* sodium pyruvate sodium thiosulfate | 75 U/plate 2.00 g/l 0.05 g/l | 114 | 0 |
| Catalase from *Scytalidium* sodium pyruvate sodium thiosulfate | 75 U/plate 0.20 g/l 0.005 g/l | 99 | 0 |
| sodium pyruvate sodium thiosulfate | 2.00 g/l 0.05 g/l | 125 | 0 |
| sodium pyruvate sodium thiosulfate | 0.20 g/l 0.005 g/l | 0 | 0 |
| without additives | | 0 | 0 |
| without additives and $H_2O_2$ | | 83 | 0 |

The combination of catalases with low concentrations of chemical additives is advantageous when compared to each component alone.

Catalases without chemical additives may lead to cracks or bubbles in agar plates with hydrogen peroxide.

Low concentrations of chemical additives without catalase, e.g. 0.2 g/l sodium pyruvate and 0.005 g/l sodium thiosulfate, did not support growth in agar plates with hydrogen peroxide.

However, the combination of a catalase with low concentrations of chemical additives, e.g. 75 U/plate catalase from *Magnaporthe* and 0.2 g/l sodium pyruvate and 0.005 g/l sodium thiosulfate, did support growth and prevented the formation of cracks and bubbles.

The invention claimed is:

1. A hydrogen-peroxide neutralizing growth medium comprising at least 0.3 U/ml of a secreted fungal catalase in admixture with a growth medium, between 0.2 g/l and 4 g/l sodium pyruvate, and between 0.005 g/l and 0.05 g/l sodium thiosulfate, wherein the growth medium is a solid agar growth medium.

2. The medium according to claim 1, wherein said medium is sterilized.

3. The medium according to claim 1, wherein said catalase is derived from a species of the genus *Magnaporthe* or *Scytalidium*.

4. The medium according to claim 3, wherein the catalase is derived from *Magnaporthe grisea* or from *Scytalidium thermophilum*.

5. The medium according to claim 1, wherein the concentration of catalase in the growth medium is between 0.3 U/ml and 90 U/ml.

6. The medium according to claim 1 wherein the concentration of sodium pyruvate in the growth medium is between 0.2 g/l and 2 g/l.

7. A method for detecting microorganisms in a hydrogen peroxide-bearing aerosol or on a hydrogen peroxide-bearing surface, said method comprising contacting said aerosol or surface with a medium according to claim 1 and detecting growth of microorganisms in said medium.

8. The method according to claim 7, comprising the steps of:
   a. bringing a hydrogen peroxide-bearing aerosol or a hydrogen peroxide-bearing surface into contact with a growth medium comprising the catalase according to claim 1;
   b. placing the growth medium in an environment allowing the development of colonies of microorganisms; and
   c. determining if colonies of microorganisms which may have developed during step (b) are present.

9. The method according to claim 7, wherein the hydrogen peroxide-bearing aerosol comprises air.

10. The method of claim 7, further comprising the step of sterilizing the medium with gamma-radiation.

* * * * *